US00PP29399P3

(12) United States Plant Patent
Kordes

(10) Patent No.: US PP29,399 P3
(45) Date of Patent: Jun. 19, 2018

(54) FLORIBUNDA ROSE PLANT NAMED 'KORFLOCI109'

(50) Latin Name: *Rosa hybrida*
Varietal Denomination: KORfloci109

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 4 days.

(21) Appl. No.: 15/330,187

(22) Filed: Aug. 19, 2016

(65) Prior Publication Data

US 2018/0054933 P1 Feb. 22, 2018

(51) Int. Cl.
*A01H 5/02* (2018.01)

(52) U.S. Cl.
USPC ..... Plt./146
CPC ..... *A01H 5/0222* (2013.01)

(58) Field of Classification Search
USPC ..... Plt./101, 102, 105, 116, 119, 123, 126, Plt./130, 135, 141, 146
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

'KORfloci109' is a new and distinct variety of *Rosa hybrida* which is characterized by the combination of a compact and upright growth habit, moderate plant vigor, very good resistance to common rose diseases, and panicles of one to five very-double orange flowers with a light fragrance. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORfloci109'.

BACKGROUND OF THE INVENTION

Parentage: The *Rosa hybrida* variety 'KORfloci109' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform, compact growth and uniform flowering; and
2. Abundant, recurrent orange flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORfloci109' from all other varieties known to the inventor.

'KORfloci109' is a seedling selection which resulted from the controlled pollination of an unnamed *Rosa hybrida* seedling developed and owned by the same inventor, the seed parent, and *Rosa hybrida* 'NOA74800' (unpatented), the pollen parent, during the summer of 2007. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2008 from the seedling beds due to its superior characteristics and asexually propagated for further evaluation. This new and distinctive rose variety was given the name 'KORfloci109'.

Asexual Reproduction: 'KORfloci109' was first asexually propagated by bud grafting in July of 2008 at the inventor's nursery in Klein Offenseth-Sparrieshoop, Germany. Subsequently, 'KORfloci109' has been successfully propagated by stem cuttings and bud grafting in Jackson County, Oreg. These initial and other subsequent propagations conducted in controlled environments demonstrate that 'KORfloci109' reproduces true to type in successive generations of asexual reproduction.

SUMMARY OF THE INVENTION

The following characteristics have been repeatedly observed and represent the distinguishing characteristics of the new *Rosa hybrida* cultivar 'KORfloci109'. These traits, in combination, distinguish 'KORfloci109' as a new and distinct cultivar.

1. *Rosa hybrida* 'KORfloci109' exhibits a moderately vigorous growth rate; and
2. *Rosa hybrida* 'KORfloci109' exhibits a compact and upright growth habit; and
3. *Rosa hybrida* 'KORfloci109' exhibits panicles bearing one to five orange flowers; and
4. *Rosa hybrida* 'KORfloci109' exhibits medium, very-double flowers with a light fragrance; and 5. *Rosa hybrida* 'KORfloci109' exhibits very good resistance to rust, black spot disease, *Botrytis* and powdery mildew.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfloci109', taken from a one year old plant.

DETAILED BOTANICAL DESCRIPTION

The following is a detailed botanical description of a new and distinct variety of *Rosa hybrida* known as 'KORfloci109', based upon observations made in August of 2016 of one year old, greenhouse-grown container plants in Jackson County, Oreg. Those skilled in the art will appreciate that certain characteristics will vary with older or, conversely, with younger plants. 'KORfloci109' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORfloci109' and comparisons with the parents and closest known comparator variety of *Rosa hybrida* are provided below.

General plant description:

*Growth rate*.—Moderately vigorous.

*Growth habit*.—Compact and upright.

*Mature dimensions*.—60 cm tall and 50 cm wide, on average.

*Cold hardiness*.—Grown successfully in USDA Hardiness Zones 6.

*Propagation*.—Stem cuttings and bud grafting.

*Disease resistance*.—Very good resistance to powdery mildew (*Sphaerotheca pannosa*), blackspot (*Diplocarpon rosae*), rust (*Phragmidium* sp.) and *Botrytis* diseases under normal growing conditions in Jackson County, Oreg.

Root system:

*Type*.—Fibrous root system.

*Branching*.—Moderately branched.

*Density*.—Moderately dense.

*Color*.—Greyed-yellow Group 161D.

*Distribution*.—Roots distributed evenly throughout the soil profile, from shallow to deep.

Stems:

*Stem color*.—Young stems are Yellow-Green Group 146A; mature stems are Yellow-Green Group 146A.

*Anthocyanin intonations*.—None present.

*Stem surface texture*.—Both young stems and mature stems are smooth.

*Stem dimensions*.—Typical mature stems are approximately 400 mm long and 9.0 mm in diameter.

*Prickles*.—Incidence — Typically 10 prickles per 10 cm of stem, on mature stems; approximately 20 small prickles per 10 cm of stem on young wood. Size — Average length is 7.0 mm long. Immature prickle color — Greyed-Orange Group N170C. Mature prickle color — Greyed-Orange Group 174B. Shape — Deeply concave. Texture — Smooth.

Leaves:

*Arrangement*.—Imparipinnate compound leaves; mature axillary leaves consisting of 7 leaflets.

*Attachment*.—Petiolate.

*Dimensions*.—120 mm long and 90 mm wide.

*Abundance*.—Average; approximately 30 to 40 leaves.

*Stipules*.—Size — 15 mm long and 5.0 mm wide. Stipule color — Yellow-Green Group 146C. Anthocyanin intonations — None present. Stipitate glands — A limited number of stipitate glands are present on the margins and on the abaxial surface. Margins — Serrulate. Texture, adaxial surfaces — Glabrous. Texture, abaxial surfaces — Leathery. Apex — Apiculate. Base — Winged.

*Petiole*.—Length — Average 10 mm. Diameter — Average 3.0 mm. Petiole color, adaxial surface — Yellow-Green Group 146C. Petiole color, abaxial surface — Yellow-Green Group 146B. Anthocyanin intonations — None present. Margins — With a few stipitate glands. Prickles — Present. Stipitate glands — A limited number of stipitate glands are present on the margins of the adaxial surface, and also on the abaxial surface. Texture — Glabrous. Strength — Strong.

*Rachis*.—Length — 20 mm. Diameter — Average 3.0 mm. Color — Yellow-Green Group 146B. Anthocyanin intonations — None present. Margins — With very few stipitate glands present. Prickles — 2 to 3 prickles underneath. Stipitate glands — A limited number of stipitate glands are present. Texture — Glabrous.

*Leaflets*.—Dimensions — Average size of the terminal leaflet is 55 mm long and 35 mm wide. Shape — Ovate. Apex — Acute. Base — Obtuse. Margins — Serrulate; no undulation. Luster, texture and pubescence; adaxial surface — Semi-glossy, leathery and glabrous. Luster, texture and pubescence; abaxial surface — Matte, leathery and glabrous. Juvenile foliage color, adaxial surface — Yellow-Green Group 146B. Juvenile foliage color, abaxial surface — Yellow-Green Group 146C. Mature foliage color, adaxial surface — Green Group 137A. Mature foliage color, abaxial surface — Yellow-Green Group 147B. Anthocyanin intonations — In juvenile foliage, intonations of Greyed-Orange Group 170A to 170B are present throughout the adaxial and abaxial surfaces. Venation — Reticulate.

*Petiolule*.—Dimensions — 2.0 mm long and 2.0 mm in diameter. Petiolule color, adaxial surface — Green Group 137A. Petiolule color, abaxial surface — Yellow-Green Group 146D. Prickles — None present. Texture, adaxial and abaxial surfaces — Leathery. Margins — With a few stipitate glands present.

Inflorescence:

*Inflorescence type*.—Panicles with 1 to 5 flower buds. Flowers are held upright to slightly pendant.

*Blooming habit*.—Recurrent; floriferous.

*Size*.—100 mm tall and 70 mm wide, on average.

*Peduncle*.—Length — 50 to 60 mm average length. Diameter — 4.0 to 6.0 mm average diameter. Color — Yellow-Green Group 146B. Anthocyanin intonations — None present. Strength — Strong. Texture and pubescence — With fine prickles, no stipitate glands, and glabrous.

Flowering laterals: Present below the initiation of inflorescence. Generally one flowering lateral is present, with 1 flower per flowering shoot.

Bud:

*Bud form*.—Short; pointed ovoid.

*Size*.—Upon opening, 30 mm in length from base of receptacle to distal end of bud and 25 mm diameter at its widest point.

*Texture*.—Smooth.

*Color, as sepals first unfold*.—Orange-Red Group 32A.

*Color when one-quarter open, inner side*.—Marginal zone — Orange-Red Group 32A. Middle zone — Orange-Red Group 32A. Basal zone — Green-Yellow Group 1A.

*Color when one-quarter open, outer side*.—Marginal zone — Orange Group 29B. Middle zone — Orange Group 29B. Basal zone — Green-Yellow Group 1A.

Flower:

*Pedicel*.—Length — 50 to 90 mm average length. Diameter — 3.0 to 5.0 mm average diameter. Color — Yellow-Green Group 146B. Anthocyanin intonations — None present. Strength — Strong to somewhat strong. Texture and pubescence — Glabrous, with numerous stipitate glands.

*Calyx*.—General — Comprised of five polysepalous sepals, with weak foliaceous appendages present on one to two of the five sepals. Diameter of calyx — 8 mm, at anthesis. Sepals — Color, upper surface — Yellow-Green Group 147C. Color, lower surface — Green Group 137C. Anthocyanin intonations — None present. Size — 30 mm long and 12 mm wide, on average. Apex — Apiculate. Base — Flat at union with receptacle. Quantity — Five. Upper surface — Moderately pubescent. Lower surface — Lightly pubescent. Margins — Pubescent with a few stipitate glands.

*Corolla*.—Habit; type — Very-double. General shape of corolla — Rosette. Shape of corolla when viewed from the side — Upon opening, upper portion — Flat. Upon opening, lower portion — Flattened convex. Open flower, upper portion — Flat. Open flower, lower portion — Concave. Dimensions — Medium size for a floribunda rose. When open, the average flower diameter is 60 to 70 mm and the average flower height is 40 mm. Fragrance — Light fruity fragrance with a slight scent of myrrh. Duration — On the plant for 5 to 6 days. Senesced petals drop away cleanly. Petals — Petal count — Exhibits very double flowers with an average of 75 petals under normal conditions. Petal reflex — Petals are strongly reflexed. Timing of petal reflex — Simultaneous. Petal margin — Entire. Petal shape — Obovate. Apex — Obtuse. Base — Obtuse. Dimensions — 25 to 30 mm long and 15 to 30 mm wide. Texture, inner surface — Smooth. Texture, outer surface — Smooth. Petal color, upon opening — Outermost petals, inner surface — Orange-Red Group 32B. Outermost petals, outer surface — Orange Group 25B to 25C. Innermost petals, inner surface — Orange-Red Group 33A. Innermost petals, outer surface — Orange-Red Group 33B. Basal petal spots, upon opening — Outermost petals — Color, inner surface — Green-Yellow Group 1B. Color, outer surface — Green-Yellow Group 1B. Dimensions — 10 mm wide and 7.0 mm tall. Innermost petals — Color, inner surface — Green-Yellow Group 1B. Color, outer surface — Green-Yellow Group 1B. Dimensions — 10 mm wide and 7.0 mm tall. Petal color, after opening — Outermost petals, inner surface — Orange-Red Group 32C. Outermost petals, outer surface — Orange Group 25C. Innermost petals, inner surface — Orange-Red Group 32B. Innermost petals, outer surface — Orange Group 29B. Basal petal spots, after opening — Outermost petals — Color, inner surface — Yellow Group 2A. Color, outer surface — Yellow Group 2B. Dimensions — 15 mm wide and 8.0 mm tall. Innermost petals — Color, inner surface — Green-Yellow Group 1A. Color, outer surface — Yellow Group 2B. Dimensions — 10 mm wide and 6.0 mm tall. General Tonality — On open flower, Orange-Red Group 32B. No change in general tonality at the end of the fourth day; thereafter the general tonality is Orange-Red Group 33C to 33D. Petaloids — Quantity — 10 to 25 petaloids per flower, on average. Dimensions — Approximately 4.0 to 8.0 mm long and 3.0 to 6.0 mm wide. Color, inner surface — Highly variable, but generally: Marginal zone — Orange-Red Group 32B. Middle zone — Orange-Red Group 32B. Basal zone — Yellow Group 3A. Color, outer surface — Marginal zone — Orange-Red Group 32B. Middle zone — Orange-Red Group 32B. Basal zone — Yellow Group 3B. Margins — Entire; reflexed. Shape — Deltoid to ovate. Apex — Obtuse. Base — Attenuate. Texture, inner and outer surfaces — Smooth.

Reproductive organs:

*Stamens*.—Quantity — Approximately 30, on average, and regularly arranged around the styles. Anthers — Shape — Reniform. Dimensions — 3.0 mm long and 2.0 mm wide, on average. Color — Greyed-Orange Group 163C. Pollen — Present; moderately abundant. Color is Greyed-Orange Group N167A. Filaments — Color — Yellow Group 9B. Length — 7.0 mm.

*Pistils*.—Quantity — Few; approximately 16. Stigmas — Size — 2.0 mm. Location — Superior in position to anthers. Color — Greyed-Yellow Group 162C. Styles — Length — Approximately 6.0 mm long. Color — Green-White Group 157B, with strong intonations of Red Group 46B.

*Ovary*.—Dimensions — 4.0 mm long and 3.0 mm in diameter. Color — White Group 155C.

*Receptacle*.—Shape — Funnel-shaped. Dimensions — Approximately 10 mm high and 6.0 mm wide. Surface texture and pubescence — Smooth and glabrous, with occasional stipitate glands. Color — Yellow-Green Group 146B.

Hips and seed formation: Not observed to date.

COMPARISONS WITH THE PARENTS

The new rose plant may be distinguished from its seed parent, an unnamed *Rosa hybrida* seedling, by the characteristics described in Chart 1.

CHART 1

| Characteristic | 'KORfloci109' | Unnamed seed parent |
|---|---|---|
| Growth habit. | Compact. | Upright. |
| Flower color. | Orange. | Yellow. |
| Flower type; petal count. | Double. | Semi-double. |

The new rose plant may be distinguished from its pollen parent, *Rosa hybrida* 'NOA74800', by the characteristics described in Chart 2.

CHART 2

| Characteristic | 'KORfloci109' | 'NOA74800' |
|---|---|---|
| Bloom period. | Medium. | Very early. |
| Flower size. | Large. | Medium. |
| Flower type; petal count. | Double. | Semi-double. |

COMPARISON WITH THE MOST SIMILAR *ROSA* CULTIVAR KNOWN TO THE INVENTOR

For a comparison, several physical characteristics of the *Rosa hybrida* variety 'KORfloci08', a rose variety from the same inventor which is described and illustrated in U.S. Plant Pat. No. 19,362, are compared to 'KORfloci109' in Chart 3.

CHART 3

| Characteristic | 'KORfloci109' | 'KORfloci08' |
|---|---|---|
| Prickle shape. | Deeply concave. | Concave. |
| Bud color as sepals unfold. | Orange-Red Group 32A. | Orange-Red Group 34A. |
| Flower type; petal count. | 60 to 70. | 40 to 45. |

That which is claimed:

1. A new and distinct variety of rose plant named 'KORfloci109', as described and illustrated herein.

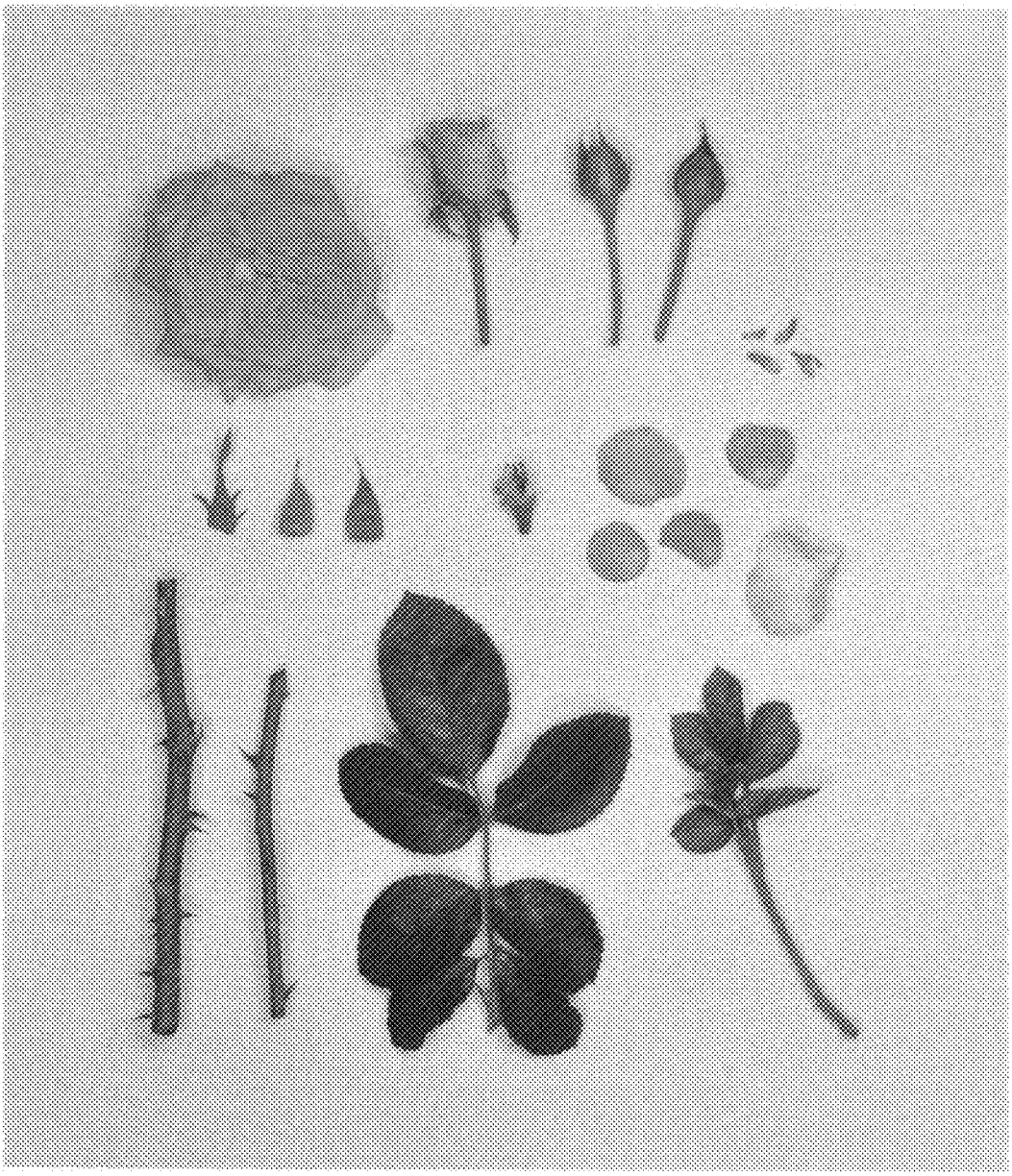

* * * * *